United States Patent [19]

Rule et al.

[11] Patent Number: 4,855,514
[45] Date of Patent: Aug. 8, 1989

[54] OXIDATIVE IODINATION OF PHENOL

[75] Inventors: Mark Rule, Kingsport, Tenn.; Regina M. Moncier, Bristol, Va.

[73] Assignee: Eastman Kodak Company, Rochester, N.Y.

[21] Appl. No.: 232,964

[22] Filed: Aug. 17, 1988

[51] Int. Cl.$^4$ .................. C07C 37/62; C07C 39/27
[52] U.S. Cl. .................................. 568/779; 568/774
[58] Field of Search ............... 568/779, 774; 570/203

[56] References Cited

U.S. PATENT DOCUMENTS 3,363,010 1/1968 Schwarzenbek .................. 568/779
4,778,940 10/1988 Rule et al. ........................ 570/203

FOREIGN PATENT DOCUMENTS 11863 6/1966 Japan ................................ 570/203

OTHER PUBLICATIONS

*J. Org. Chem.,* vol. 35, No. 10, 1970, "Halogenation with Copper (II) Halides, The Synthesis of Aryl Iodides".
*Bulletin of the Chemical Society of Japan,* vol. 47(1), (1971), "Aromatic Bromination and Iodination with Mixtures of Antimony (V) Chloride and Halogens".
*Fieser and Fieser,* vol. 1 (1967).

*Primary Examiner*—Werren B. Lone
*Attorney, Agent, or Firm*—Charles R. Martin; William P. Heath, Jr.

[57] ABSTRACT

A process for producing iodophenols which comprises contacting phenol, a source of iodine and molecular oxygen in an aqueous medium to produce an iodophenol.

2 Claims, No Drawings

OXIDATIVE IODINATION OF PHENOL

This invention relate to a process wherein phenol, elemental iodine and molecular oxygen are contacted to produce an iodinated phenol.

A variety of methods have been developed for the iodination of activated aromatics compounds. For example, iodine-thallium(I) acetate, iodine-mercury(II) acetate, iodine-silver(I) acetate, iodine-copper(II) acetate, and sodium iodide-sodium hypochlorite systems have been discussed in the patent and chemical literature as methods for the production of iodophenols from phenol. These methods suffer from the disadvantage that a stoichiometric amount of an oxidant is required to drive the reaction to completion. Although phenol will react with elemental iodine to form iodophenol in the absence of other reagents, the reaction normally will only proceed to 20%–30% conversion. Presumably the reaction ceases due to the formation of $HI_3$, which is less reactive than $I_2$. Therefore, it would be an advance in the state of the art to provide a process whereby the idodination of phenol could be carried essentially to completion without the utilization of an expensive oxidant.

We have now found that the iodination of phenol can be carried out by contacting phenol, a source of iodine, and molecular oxygen at elevated temperatures and pressures, using water as the reaction solvent. Under the conditions of our process, the conversion of iodine is essentially quantitative.

The temperature required for this reaction is between 100° C. and 200° C. At temperatures below 100° C. the reaction rate becomes unacceptably slow. At temperatures above 200° C. the reaction pressure becomes unacceptably high; also, at temperatures above 200° C. decomposition of the product idophenols becomes significant. A preferred temperature range is from 125° C. to 175° C.

The molecular oxygen can be provided to the reaction as air, depleted air, enriched air, or as pure oxygen. Since the reaction solvent is water, the use of enriched air or pure oxygen is much less hazardous than if organic solvents were employed. An advantage for the use of enriched air or pure oxygen is the lower total reaction pressure and lower scrubbing requirements over air or depleted air as the oxidant. However, all sources of molecular oxygen fall within the scope of this invention.

The reaction pressure will depend in part on the reaction temperature, but in general the partial pressure of molecular oxygen should be between 10 and 1,000 psia, preferably between 25 and 500 psia.

The concentrations of reactants, especially phenol, is quite critical. When the concentration of phenol is greater than about 25 weight %, based on the total weight of phenol, water and iodine, essentially no oxygen uptake occurs and conversion on iodine is unacceptably low. When the concentration on phenol is less than 15 weight %, on the same basis, oxygen uptake is rapid at 125° C. At lower concentrations of phenol, the rate of oxygen uptake is even more rapid. Therefore, the range of concentration for phenol is from 15 to 1, preferably 13 to 3 weight %, based on the total weight of the phenol, water and iodine.

The concentration of iodine in the reaction should be adjusted to maximize the amount of desired iodophenol produced in the reaction. Although higher concentrations of iodine are not detrimental to the reaction, they result in the preferential formation of di- and tri-iodophenols, which often are not the desired reaction product. To minimize the formation of polyiodophenols and maximize the formation of monoiodophenols, the ratio of iodine to phenol should be less than 0.5. Under the conditions of our reaction, the ratio of para to ortho iodophenol is near 1; that is the amount of p-iodophenol and o-iodophenol are nearly equal. No m-iodophenol has been detected as a product of our reaction. Both the ortho and para iodophenols are useful intermediates for the production of a number of useful chemicals, such as salicylic acid, p-hydroxybenzoic acid, p-aminophenol, and the like.

Separation of the iodophenol isomers may be accomplished by a variety of techniques, such as iodophenol isomers may be accomplished by a variety of techniques, such as vacuum distillation or low-temperature crystallization.

Sources of iodine suitable for the present reaction include elemental iodine, hydriodic acid, and iodoalkanes. Elemental iodine is perferred.

An unexpected advantage of the use of water as a reaction solvent in this process is that the iodophenols separate as a layer on cooling the reaction mixture, thus making isolation of the reaction product straightforward. The recovery of iodophenols from other reaction solvents is difficult and costly, due to the high solubility of iodophenols in organic solvents.

EXAMPLES

In the following examples, the indicated amounts of reactants were placed in a 330-mL Hastelloy C autoclave under the specified conditions. The reaction products were analyzed by gas chromatographic analysis and the reaction conversions calculated by the GC analysis and independently by the reaction pressure drop. All product analyses are in weight % unless otherwise noted.

EXAMPLE 1

10 grams phenol
100 grams water
13 grams iodine
125° C.
200 psi air
one hour

By GC analysis, there was 87% conversion to iodophenols based on iodine. By pressure drop the conversion was 85%.

EXAMPLE 2

10 grams phenol
100 grams water
13 grams iodine
75° C.
200 psi air
one hour

By GC analysis, the conversion to iodophenols was less than 10%. No oxygen uptake was observed as measured by the drop in reaction pressure.

EXAMPLE 3

10 grams phenol
100 grams water
14 grams iodomethane
125° C.
400 psi air two hours The reaction pressure drop ceased after 90 minutes (130 psi total drop). The organic layer was analyzed by liquid chromatography. Findings were 37.0 weight % p-iodophenol, 25.5 weight % o-iodophenol, and no m-iodophenol (detection limit 10 ppm). GC-MS found no methyl substituted phenolic products. The aqueous layer contained 3% methanol.

EXAMPLE 4

10 grams phenol
100 grams water
13 grams iodine
150° C.
400 psi air
two hours

The reaction pressure drop ceased after less than one hour (80 psi total drop). The organic layer was analyzed by GC. Findings were 9.7% phenol, 30.7% p-iodophenol, 24.0% o-iodophenol, and 35.5% diiodophenols. Iodine conversion was >98%.

EXAMPLE 5

25 grams phenol
100 grams water
17 grams iodine
140° C.
400 psi air
four hours

The product mixture contained iodophenols and diiodophenols. Conversion was 54% based GC yield; however, no oxygen uptake was noted and the reaction mixture was homogeneous (no separation of organic products). This example shows the deleterious effect of higher phenol concentrations on the oxygen uptake.

EXAMPLE 6

10 grams phenol
100 grams water
6.5 grams iodine
125° C.
400 psi air
two hours

The reaction product was 47.3% phenol, 24.85% o-iodophenol, 23.8% p-iodophenol, and 4.2% diiodophenols (GC area %).

EXAMPLE 7

10 grams phenol
100 grams water
6.5 grams iodine
150° C.
400 psi air
two hours

The reaction product was 44% phenol, 27% o-iodophenol, 24.4% p-iodophenol, and 1.8% diiodophenols (GC area %).

The process of this invention has been described in terms of specific embodiments; however, it will be understood that variations and modifications can be made which will be within the scope of the invention.

What is claimed is:

1. A process for producing iodophenols which comprises contacting phenol, a source of iodine selected from the group consisting of elemental iodine, hydriodic acid and iodoalkanes and molecular oxygen in an aqueous medium at a temperature in the range of 100 degrees to 200 degrees C. and a pressure in the range of 10 to 1,000 psia.

2. A process for producing iodophenols which comprises contacting phenol, elemental iodine and molecular oxygen in an aqueous medium at a temperature in the range of 125° to 175° C. and a pressure in the range of 25 to 500 psia.

* * * * *